United States Patent [19]

Steinke et al.

[11] 4,187,163
[45] Feb. 5, 1980

[54] ELECTROCHEMICAL EXHAUST GAS OXYGEN SENSOR CONSTRUCTION

[75] Inventors: Leo Steinke, Waiblingen; Helmut Weyl, Schwieberdingen, both of Fed. Rep. of Germany

[73] Assignee: Robert Bosch GmbH, Stuttgart, Fed. Rep. of Germany

[21] Appl. No.: 863,612

[22] Filed: Dec. 23, 1977

[30] Foreign Application Priority Data

Jan. 22, 1977 [DE] Fed. Rep. of Germany ....... 2702578

[51] Int. Cl.² ............................................. G01N 27/46
[52] U.S. Cl. .......................... 204/195 S; 123/119 E; 73/23; 55/385 F; 204/1 IT
[58] Field of Search ............... 204/1 S, 195 S; 123/119 E; 73/23, 27 R, 26, 421.5 R; 55/385 F

[56] References Cited

U.S. PATENT DOCUMENTS

| | | | |
|---|---|---|---|
| 2,721,619 | 10/1955 | Cheairs | 55/385 F |
| 2,747,101 | 5/1956 | Hammond | 55/385 G |
| 3,698,159 | 10/1972 | Ruse | 73/23 |
| 3,822,581 | 7/1974 | Hauck et al. | 73/23 |
| 3,960,693 | 6/1976 | Weyl et al. | 204/195 S |
| 4,019,974 | 4/1977 | Weyl et al. | 204/195 S |
| 4,088,555 | 5/1978 | Kita et al. | 204/195 S |

FOREIGN PATENT DOCUMENTS 2504207 8/1976 Fed. Rep. of Germany .

*Primary Examiner*—T. Tung
*Attorney, Agent, or Firm*—Frishauf, Holtz, Goodman & Woodward

[57] ABSTRACT

To prevent ingress of moisture, water, dirt, or other contamination into the interior of an exhaust gas sensor having an opening to provide for communication with ambient air to establish an oxygen reference level, a cover cap, preferably of metal, but which may be of plastic if extreme heat resistance is not required, is placed over the sensor, the cover cap being formed with a labyrinth which provides for communication between ambient air and the interior of the sensor, the labyrinth preferably being formed as a groove, especially a spiral groove, in the interior of the cap and having access to outside ambient air, the cap preferably being secured by means other than friction, such as a spot weld, an engagement catch or the like to the sensor housing.

10 Claims, 2 Drawing Figures

U.S. Patent  Feb. 5, 1980  4,187,163
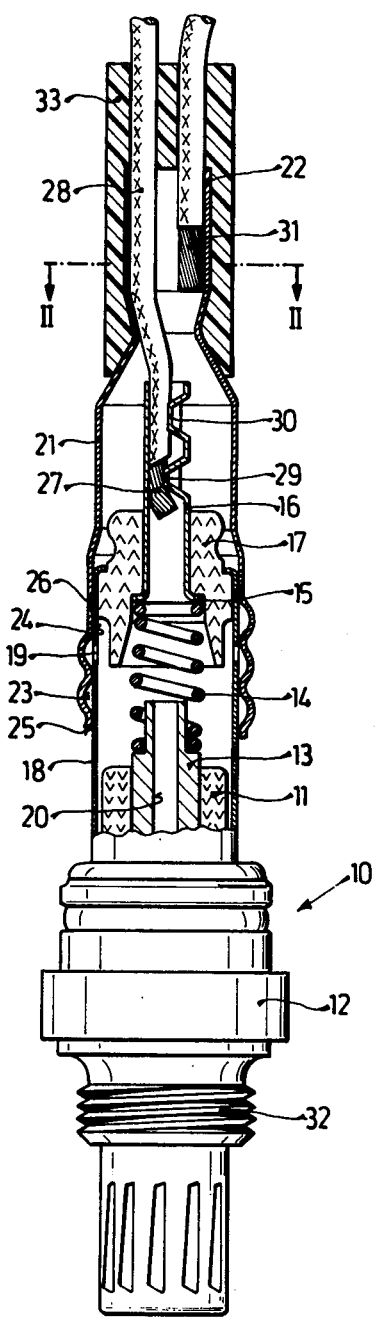
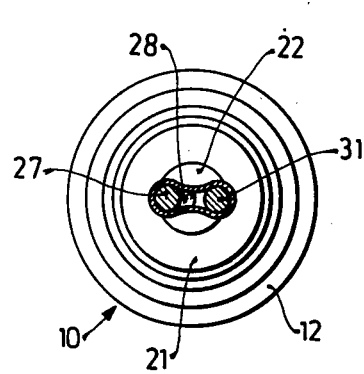

ELECTROCHEMICAL EXHAUST GAS OXYGEN SENSOR CONSTRUCTION

Cross reference to related patent in this field, assigned to the assignee of the present application: U.S. Pat. No. 4,019,974, WEYL et al.

The present invention relates to an electrochemical sensor, and more particularly to an exhaust gas sensor to determine presence of oxygen in the exhaust gases from internal combustion engines, so that the air-fuel ratio of the air-fuel mixture being supplied to the engine can be controlled as a function of the output signal from the sensor.

Electrochemical sensors have previously been proposed, in which a closed tube of a sensing substance, typically a zirconium oxide tube, is exposed to the exhaust gases from an internal combustion engine. The sensing tube, forming a solid electrolyte body, is exposed at the outside to the exhaust gases, the inside thereof being in communication with ambient air so that the oxygen in the ambient air can form a reference oxygen level. These elements are physically secured to sockets which can be screwed or otherwise secured to the exhaust system of an internal combustion engine, typically of an automotive internal combustion engine, such that the electrolyte tube is exposed to the exhaust gases. The socket is provided with an opening at the outside to permit ingress of ambient air. It is necessary to shield the socket against contamination of the interior of the sensor.

It has previously been proposed to provide a cover cap for the sensor housing extending outside of the exhaust system, the cover cap being made of rubber and overlapping the air inlet opening for the reference oxygen level with a little clearance (see, for example, U.S. Pat. No. 3,960,693). Such cover caps are subject to deterioration by heat; furthermore, in long use, the may not reliably prevent the ingress of water, dirt, and the like, into the interior of the sensor.

THE INVENTION

It is an object to provide a sensor construction in which the sensor has a cover cap which is so designed that it can be heat-resistant and additionally reliably prevents ingress of dirt or contamination to the interior of the sensor over an extended period of time, even under the rough environmental conditions of the exhaust system of an automotive vehicle.

Briefly, the cover cap includes a narrow labyrinth, preferably in form of a spiral groove, the cap being tightly and snugly engaged over the end or socket portion of the sensor, the groove forming the labyrinth being in communication with ambient air at one end and, at the inner one, in communication with an opening through the socket of the sensor to provide for gas communication between the interior of the sensor and ambient air. Such a cover cap can be made of metal if heat resistance is required, or of plastic. It is preferably connected to the socket of the cover cap, for example by welding, if made of metal, or by other suitable connection. The engagement surface of the socket with the cover cap can be smooth; it is not threaded, however, to match the spiral groove in the cover cap, the spiral groove forming an air duct or air channel, over a tortuous path, but not the connection of the cap with the sensor housing, the mechanical connection between the cap and the sensor housing being otherwise established.

The sensor structure has the specific advantage that water, dirt, or other contamination which frequently arises in the environment of automotive vehicles is reliably prevented from reaching the interior of the sensor. The sensor cap further permits an electrical connection to the chassis or ground terminal of the sensor to be made simply and inexpensively. The structure is versatile and can be used with various materials having required heat resistance, in accordance with the design requirements of the location of the sensor in an automotive vehicle engine system.

Drawings, illustrating an example:

FIG. 1 is a longitudinal view in which the elements material for the present invention are shown in section, and to an enlarged scale; and FIG. 2 is a cross-sectional view, to a still greater scale, along line II—II of FIG. 1, in which the sectional representation of the sealing element has been omitted.

The basic principle of the sensor of FIGS. 1 and 2 is known; a solid ion conductive electrolyte tube 11, preferably a tube closed at one end is provided, exposed to exhaust gases from an internal combustion engine. The outside of the solid electrolyte tube, exposed to the exhaust gases, is covered at least in part with a catalytically active, electron-conductive layer, for example platinum. The inside of the solid electrolyte tube, closed at the end exposed to the gases, is in gas communication with ambient air, forming a reference oxygen level therefor. The solid electrolyte body 11 is held in a metallic socket 12 which is electrically connected to the electron conductive layer at the outside of the solid electrolyte body, and forms the ground or chassis terminal of the system. In other constructions, a separate lead may be brought out, connected to the outer platinum coating, for a separate ground connection. In the embodiment shown, however, the outer platinum layer is connected to the socket made of metal. The inside of the solid electrolyte body 11 has a contact surface applied thereto, the electrical voltage of which is taken therefrom by means of a connecting sleeve 13 which is electrically connected to a spring 14, providing both for resilience meating of the tube 11 against a counter flange (not shown) and for electrical connection to the interior of the solid electrolyte tube 11. The construction of the sensor essentially corresponds to German Disclosure Document DT-OS 2,504,207. Reference is made to U.S. Pat. No. 4,019,974, which shows a similar construction, and which may be used if it is desired to separate the outer conductor on the solid electrolyte tube electrically from the chassis connection to the sensor housing. The upper portion of the connecting element 13, forming a tubular sleeve of conductive material, is offset to form a guide tube for the spring 14. Spring 14 is a spiral spring which extends with its upper end against a flange 15 of a metallic contact tube 16. Contact tube 16 is held in a insulating bushing 17, for example of ceramic or ceramic-like material. The bushing 17 is secured in a tubular end portion 18 of the sensor housing 12, for example by being held by an inturned edge fitting into a groove, or against a shoulder thereof. The tubular end 18 is formed with several transversely extending openings 19 which permit ingress of external ambient air into the interior of the sensor 10, and specifically to the interior of the solid electrolyte tube 11 through the longitudinal opening 20 in the connecting sleeve 13.

It is important that only air is permitted to enter the interior of the sensor tube 11, and that water, moisture or any other contamination is reliably prevented from reaching the interior of the tube 11, and preferably even from reaching the interior of the housing tube 18. In accordance with the invention, a cover cap 21 is provided which coaxially engages the housing tube 18 and which is formed, at the inner side and at the end covering the tube 18, with a spiral groove to form a narrow labyrinth 23. The inner diameter of the cap 21 fits snugly against tube 18. The grooved portion of the cap extends from the end 25 of the cap up to the region where the transverse openings 19 are placed in the housing portion 18 of the sensor itself. The other end of the cap 21 terminates in a tubular stub 22 which has openings to permit passage of connecting lines therethrough. More than a single groove 21 can be formed in the end of the cap 21 adjacent the openings 19, or the labyrinth may be formed not by spiral grooves but rather by differently shaped narrow depressions punched, rolled, or otherwise formed in the cap 21. Regardless of how made or formed, a tortuous path should be provided to permit air communication between ambient air and the openings 19 while, at the same time, rejecting splashed water, or ingress of any other contamination. The groove 23 terminates slightly above the location of the openings 19 and the remainder of the cap 21 snugly engages the adjacent region of the tubular end 18 of the socket of the sensor. In a preferred form, the cap is made of a thin-gauge metal and secured against removal from the socket by a weld, for example a spot weld 26. Other known connection methods, such as screws, adhesives, or other bonding processes may be used. The groove 23 having the tortuous path forms a trap or labyrinth in advance of the transverse openings 19 which reliably ensures rejection of dirt, water, or other contaminants, and their ingress into the interior of the sensor 10.

At least one conductor 27 extends through the tubular end 22 of the cap 21. The end portion of the conductor 27, which is insulated, is stripped and electrically connnected to the connecting tube 16 by a pressure engagement, for example formed by a punch 29. A second punch 30, of lesser depth, is used to mechanically secure the conductor 27 in the connecting tube 16, the second deformation 30 merely clamping the insulated conductor in the tube 16 to form a strain relief. An additional strain relief is provided by either the cap 21, or a cover cap, if the cap 21 can be made of a material which is subject to permanent deformation so that the conductor 28 is securely connected in the cap 21. This arrangement is particularly suitable if the cap 21 is made of a thin sheet metal, engagement of the insulation 28 of conductor 27 by the cap 21 being best seen in FIG. 2. If cap 21 is made of metal, the additional advantage pertains that the tubular extension 22 can simultaneously form an excellent connecting element for the ground or chassis connection of the sensor. A separate ground or chassis conductor 31 can be connected to the sensor 10. The conductor 31 can be a separate conductor—as shown—or can be a coaxial metal braiding over the insulation 28 of conductor 27, and then electrically secured to tube 21 by deformation of the tubular end 22, simultaneously providing for mechanical as well as for electrical connection of the ground conductor. Alternatively, the ground conductor 31 can be soldered, spot-welded, or otherwise suitably connected as shown in FIGS. 1 and 2. A separate additional ground line 31 is frequently desirable since it ensures an exact and precise ground connection also in such cases in which the ground connection through housing 12 of the sensor and the associated thread 32 formed on the housing is not in good electrical contact with the exhaust pipe in which the sensor is secured. Since these exhaust pipes are subject to high temperatures, corrosion is a persistent problem and the electrical connection is preferably provided by a separate conductor also for the ground or chassis or reference terminal of the sensor.

An external sealing element 33 is slipped over the tubular end 22 of cap 21. The sealing element 33 snugly engages the outsides of conductors 27, 31 and ensures protection against contamination, dirt, water, and the like. The sealing element 33 preferably is an elastic cap made, for example, of silicone rubber; a plastic; or similar material. It is snapped into a slight groove formed between the junction of the end portion 22 and tube 21, as best seen in FIG. 1.

If the cap 21 is not needed as a ground connection, and the heat loading thereon is not excessive, cap 21 can be made of a heat-resistant plastic. If the sensor 10 is to be placed in an exhaust portion of the exhaust system of the engine close to the engine block, then forming cap 21 of metal is recommended to provide a clearly heat-resistant material for the cap. Caps made of plastic can be made as injection-molded articles; caps made of metal, by rolling and folding of a metal strip, or by deep drawing of a blank, in accordance with well-known metal working procedures.

The connection between cap 21 and the tubular portion 18 of the housing of the sensor preferably is non-removable, for example by spot welds 26, as shown. In some installations, and for some purposes, it may be sufficient to provide releasable connections, for example by deforming the tube 18 or the cap portion 21 to form a snap engagement, by punching out a lip on one part which engages into an opening or a depression on the other; or by other suitable connections. If a connection other than welding, brazing, or soldering is used, then the burr from a deformation operation need not be removed, since the burr can bite into the material of the other part to ensure a good electrical contact throughout the life of the unit.

Various changes and modifications may be made within the scope of the inventive concept.

We claim:

1. Electrochemical sensor for exposure to the exhaust gases of an internal combustion engine to determine the oxygen content therein having a socket (12);

a solid electrolyte tubular body (11) located in the socket (12);

electrical connection means (14, 15, 16, 27) electrically connected to an electrode on the inside of the tubular body (11);

said socket including a tubular portion (18) extending in the direction of the open end of the tubular body (11) and being formed with at least one opening (19) in gas communication with ambient air to permit penetration of ambient air to reach the interior of said tubular body (11) and provide a reference oxygen level in the interior of the tubular body; and a cap (21) extending axially over said tubular portion (18) to protect the interior thereof against ingress of contamination, wherein, in accordance with the invention, said cap (21) fits snugly about the outer surface of the tubular portion (18) of the socket (12) and extends over said at least one opening (19) and is formed at its interior surface facing the tubular portion with a continuous recess extending in a labyrinthine or tortuous path formed between the outside of the tubular portion (18) of the socket (12) and the interior surface of the cap (21) and in gas communication with ambient air and with said at least one opening (19) to permit entry of air into the interior of the socket only through said labyrinthine or tortuous path between said cap and the socket while excluding contamination from the interior of the socket.

2. Sensor according to claim 1, wherein said labyrinthine or tortuous path comprises a spiral groove formed in the interior surface of the cap.

3. Sensor according to claim 1, wherein said labyrinthine or tortuous path comprises at least one spiral groove formed in the interior surface of said cap (21), terminating at a free end portion of the cap to be in gas communication with ambient air and in gas communication with said at least one opening; and wherein the ungrooved inner surface of the cap (21) fits snugly about the outer surface of said tubular portion (18).

4. Sensor according to claim 1, wherein the cap is a thin-walled metal element (21) bonded to the socket (12, 18).

5. Sensor according to claim 1, wherein the cap is a thin-walled metal element welded to the tubular portion (18) of the socket.

6. Sensor according to claim 1, wherein said cap has a tubular extension (22); and at least one connecting conductor (27, 31) extending through said tubular extension.

7. Sensor according to claim 6, wherein said tubular extension (22) is deformed in the region where said at least one connecting conductor (27, 31) passes therethrough, the deformed portion of said tubular extension securely gripping the connecting conductor to form a mechanical holding connection therefor.

8. Sensor according to claim 7, wherein the outside of said body (11) is electrically connected to said socket;

the cap (21) is of metal, and electrically connected to the tubular portion (18); and two electrical conductors (27, 31) pass through the tubular extension (22), one conductor being electrically connected to said tubular extension (22) to form a ground or chassis conductor, the other connecting conductor (27) being the reference conductor and forming part of said electrical connection means.

9. Sensor according to claim 6, further including a cover cap (33) of elastic material closing off the tubular portion (22) of the cap (21) and sealingly surrounding said at least one connecting conductor (27, 31).

10. Sensor according to claim 9, wherein said cover cap is made of a material comprising at least one of: an elastomer; a plastic material; a heat-resistant elastic plastic material; silicone rubber.

* * * * *